May 30, 1972 W. E. LAMMERTS Plant Pat. 3,203
ROSE PLANT
Filed Nov. 10, 1970
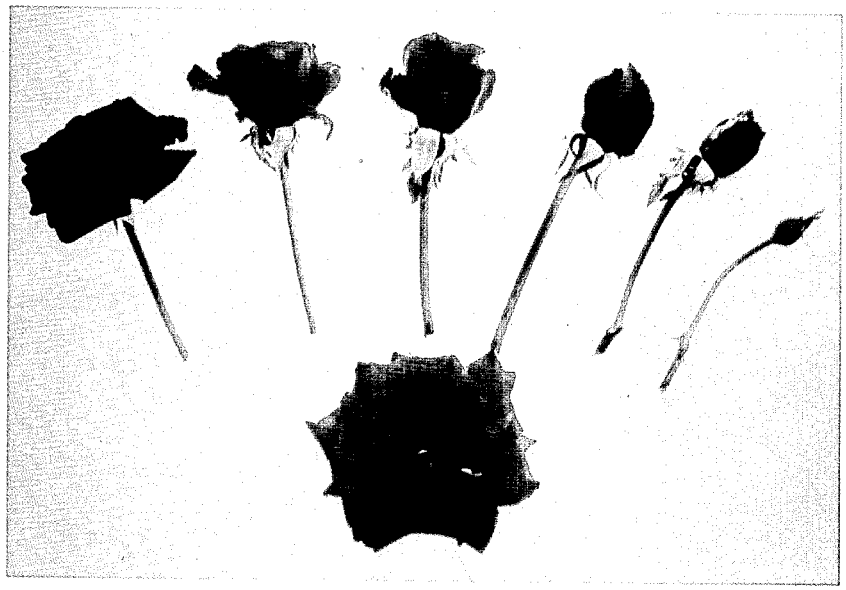
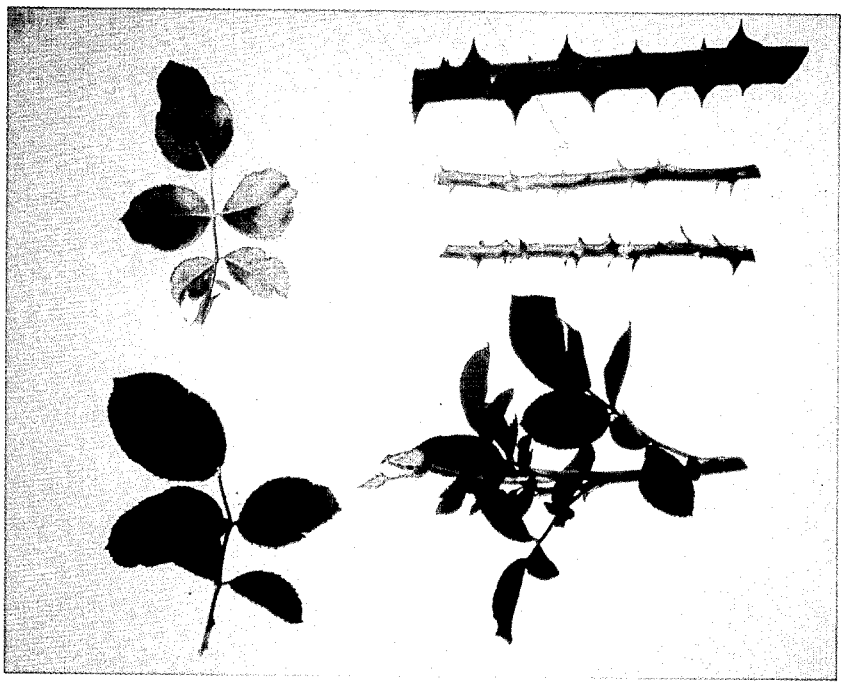
Inventor.
W. E. Lammerts
By: Robb & Robb
Attorneys.

United States Patent Office

Plant Pat. 3,203
Patented May 30, 1972

3,203

ROSE PLANT

Walter E. Lammerts, Watsonville, Calif., assignor to Devor Nurseries, Inc., Livermore, Calif.

Filed Nov. 10, 1970, Ser. No. 88,526
Int. Cl. A01h *5/00*
U.S. Cl. Plt.—21 1 Claim The present invention relates to a new and distinct variety of rose plant of the hybrid tea class, which was originated by me by crossing the rose variety known as "Baccara" (Plant Patent No. 1,367) with an unnamed and unpatented seedling of "Queen Elizabeth" (Plant Patent No. 1,259) × "Red Delight" (unpatented), the former being the seed parent and the latter being the pollen parent.

As the result of this breeding, I have produced a new and improved rose variety which is distinguished from its parents, as well as from all other rose varieties of which I am aware, as evidenced by the following unique combination of characteristics which are outstanding in the new variety:

(1) A very upright and vigorous plant habit;
(2) Large, leathery and attractive dark green mature-foliage;
(3) Moderate sized buds and blooms which are usually borne in candelabra arrangement, said buds being of urn-shaped form and opening to high-centered blooms which show the stamens when the blooms reach a finishing wide-open stage;
(4) Good flower petalage, with the petals having a heavy substance; and
(5) A distinctive and attractive dark red flower color which is often striated with lighter and darker shades or red color.

In comparison with the parent variety "Baccara," my new variety bears larger flowers, and the flowers are a deep, dark red color, whereas those of "Baccara" are a bright orange red color; the flower petals of the new variety are fewer in number; and the petals reflex less as the flowers unfold.

My new rose variety most nearly resembles the variety known as "Scarlet Knight" (Plant Patent No. 2,692), but the plants of the new variety have almost no bristles or prickles, while those of "Scarlet Knight" have many prickles; the thorns are straighter and not hooked; the foliage is larger, heavier, more leathery, more glossy and darker green in color; the buds are urn-shaped while those of "Scarlet Knight" are oval; the petals have a much heavier substance, are more reflexed and the sepals are more foliar; the dark red bud color is more striated; the petlage of the new variety is slightly less and the open blooms maintain a high center, while those of "Scarlet Knight" are often low-centered; the petals are oval in shape while those of "Scarlet Knight" are almost round; the stamen filaments are dark red in color as compared with the light red and yellow of those of "Scarlet Knight"; and the flowers hold their darker red color as the blooms finish.

Asexual reproduction of my new variety by budding, as performed by me at Livermore, Calif., shows that the foregoing characteristics and distinctions come true to form and are etsablished and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with the Horticultural Colour Chart of the British Colour Council, except where general color terms of ordinary dictionary significance are obvious, as based upon observations of specimens grown at Shafter, Calif.:

Type: Hardy; tall; outdoor; seedling; for cut flowers and for garden decoration.
Class: Hybrid tea.
Breeding: Seedling.
*Seed parent.*—"Baccara."
*Pollen parent.*—An unnamed seedling of "Queen Elizabeth" × "Red Delight."
Propagation: Holds its distinguishing characteristics through succeeding propagations by budding.

*Flower*

Flowers borne: Sometimes singly, but usually three or more to stem; on strong, medium long stems.
Quantity of bloom: Abundant, outdoors.
Continuity: Continuous.
Fragrance: Moderate. Nature—spicy.
Bud:
*Peduncle.*—Long; medium heavy; stiff; almost smooth; few red hairs. Color—dark reddish.
*Before calyx breaks.*—Size—medium. Form—pointed; oval; sometimes with foliaceous parts extending beyond the tip of the bud equal to ¼ or more or more of its length; slender and cut at base; top half rounded. Color—Pod Green, Plate 061, with Erythrite Red, Plate 0027.
*As calyx breaks.*—Color—Pod Green, Plate 061/1, with Erythrite Red, Plate 0027/1.
*As first petal opens.*—Size—medium. Form—ovoid. Color—outside—Chrysanthemum Crimson, Plate 824/2. Inside—Cardinal Red, Plate 822.
*Opening.*—Opens up well.
Bloom:
*Size (when fully open).*—Medium; from 3 inches to 4 inches.
*Petalage.*—Very double; from 30 to 35 petals; arranged regularly.
*Form.*—High-centered, but becoming open; petals at first being rolled outward and remaining rolled outward at maturity.
Petals:
*Texture.*—Thick.
*Appearance.*—Inside—velvety—outside—satiny.
*Shape.*—Outside—round. Intermediate—round, with 1 notch. Inside—ovate, with 3 notches.

This description of a newly opened flower was made from a rose grown outdoors during the month of May at Shafter, Calif.:

*Color.*—Outer petal—Outside surface—Indian Lake, Plate 826/1. Inside surface—Cardinal Red, Plate 822/1. Intermediate petal—Outside surface—Chrysanthemum Crimson, Plate 824/3. Inside surface—Cardinal Red, Plate 822/2. Inner petal—Outside surface—Indian Lake, Plate 826. Inside surface—Indian Lake, Plate 826/1.

This description was made from a rose that was open for three days outdoors during the month of May at Shafter, California:

*Color.*—Outer petal—Outer surface—Ruby Red, Plate 827. Inner surface—Indian Lake, Plate 826/1. Inner petal—Outside surface—Cardinal Red, Plate 822/3. Inside surface—Cardinal Red, Plate 822/2.
*General color effect.*—Newly opened flower—Cardinal Red, Plate 822. Three days open—Cardinal Red, Plate 822/3.
*Behavior.*—Hot weather causes greater contrast between Chrysanthemum Crimson and Cardinal Red colors.

*Flower longevity.*—On bush in garden—4 days in May. Cut roses grown outdoors and kept at living-room temperatures—6 days in May.

*Reproductive organs*

Stamens: Medium number; arranged regularly about pistils. Color—Yellow.
Filaments: Medium length; most with anthers. Color—Yellow.
Anthers: Medium large: open at various times. Color—Yellow.
Pollen: Moderate quantity. Color—Gold.
Pistils: Medium number.
Styles: Uneven.
Stigma: Color—White.
Ovaries: All enclosed in calyx.
Hips: None observed.
Sepals: None observed.
Seeds: None observed.

*Plant*

Foliage:

*Leaves.*—Compound of 5 leaflets; normal abundance; medium large size; heavy.

*Leaflets.*—Shape—oval. Apex—obtuse—mucronate. Base—obtuse. Margin—doubly serrate.

*Color.*—Mature—Upper surface—normal green. Under surface—light green. Young—Upper surface—moderately dark greenish bronze. Under surface—light greenish bronze.

*Rachis (the supporting stem of the compound leaf).*—Medium caliper. Upper side—smooth. Under side—smooth.

*Stipules.*—Moderately short; narrow; with points of medium length turning out at an angle of more or less than 45°.

Growth:

*Habit.*—Upright.

*Growth.*—Vigorous.

*Canes.*—Medium caliper.

*Main stems.*—Color—green. *Thorns*—several; medium length; straight; with long, narrow base. *Prickles*—few. Color—grey. *Hairs*—none.

*Branches.*—Color—bright greenish bronze. *Thorns*—several; medium length; straight; with long, narrow base. *Prickles*—few. Color—reddish. *Hairs*—none.

*New shoots.*—Color—bright bronze red. *Thorns*—several; medium length; straight; with narrow base. *Prickles*—few. Color—reddish. Hairs—none.

I claim:

1. A new and distinct variety of rose plant of the hybrid tea class, substantially as herein shown and described, characterized particularly as to novelty by the unique combination of a very upright and vigorous plant habit, large leathery and attractive dark green mature foliage, moderate sized buds and blooms which are usually borne in candelabra arrangement, said buds being of urn-shaped form and opening to high-centered blooms which show the stamens when the blooms reach a finishing wide-open stage, good flower petalage, with the petals having a heavy substance, and a distinctive and attractive dark red flower color which is often striated with lighter and darker shades of red color.

No references cited.

ROBERT BAGWILL, Primary Examiner